US00PP18579P2

(12) United States Plant Patent
Sanders

(10) Patent No.: US PP18,579 P2
(45) Date of Patent: Mar. 11, 2008

(54) ***IMPATIENS* PLANT NAMED 'IMTRACARO'**

(50) Latin Name: *Impatiens walleriana*
Varietal Denomination: Imtracaro

(75) Inventor: Monica Maria Adelheid Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/585,729

(22) Filed: Oct. 24, 2006

(51) Int. Cl.
*A01H 5/00* (2006.01)

(52) U.S. Cl. ..... Plt./317

(58) Field of Classification Search ..... Plt./317
See application file for complete search history.

*Primary Examiner*—Kent Bell
*Assistant Examiner*—Louanne Krawczewicz Myers
(74) *Attorney, Agent, or Firm*—Bruce Vrana

(57) ABSTRACT

A new *Impatiens* plant, characterized particularly as to novelty by a flat and strong outward spreading growth habit, freely branching with branches that tend to grow horizontally, resulting in a big and floriferous plant with light rose flowers.

1 Drawing Sheet

Latin name of the genus and species of the plant claimed: *Impatiens walleriana.*
Varietal denomination: 'Imtracaro'.

BACKGROUND OF THE NEW PLANT

The present invention comprises a new distinct cultivar of *Impatiens,* botanically known as *Impatiens walleriana.*

The new *Impatiens* is a product of a planned breeding program conducted in Enkhuizen, Netherlands. The new *Impatiens* cultivar has a flat and spreading growing type, is floriferous with large flowers, and has attractive foliage.

The present cultivar originated from a cross-pollination made in 2002, of a proprietary *Impatiens walleriana* selection identified as 'S3408-1,' not patented, as the female, or seed parent, with a proprietary *Impatiens walleriana* selection identified as 'S2012-1,' not patented, as the male, or pollen parent.

The present cultivar has been repeatedly asexually reproduced by cuttings in Enkhuizen, Netherlands, in Angers, France, and in Gilroy, Calif., USA over a four year period. The new variety is stable and reproduces true to type in successive generations of asexual reproduction. It takes 6 to 8 weeks to produce a finished plant, depending on the temperature.

The new *Impatiens* plant is an annual in most climatical zones in the US, only in zones 9 and 10 it is a perennial plant.

DESCRIPTION OF THE DRAWING

This new *Impatiens* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new *Impatiens.* The data which defines these characteristics were collected from asexual reproductions carried out in Enkhuizen, Netherlands. The plant history was taken on 27 week old plants blossomed under natural light in the field.

Color readings were taken in the office under ambient light. Color references are primarily to the R.H.S. Colour Chart of The Royal Horticultural Society of London.

Plants of the new *Impatiens* differ primarily from the plants of the female parent selection in the following characteristics:

Plants of the new *Impatiens* have light rose flowers and a good trailing habit, whereas the plants of the female parent have orange flowers.

Plants of the new *Impatiens* differ primarily from the male plant selection in the following characteristics:

Plants of the new *Impatiens* have light rose flowers, whereas the plants of the male parent have light salmon flowers.

TABLE 1

DIFFERENCES BETWEEN THE NEW CULTIVAR 'IMTRACARO' AND A SIMILAR CULTIVAR

| | 'Imtracaro' | 'Imtrarose' (U.S. Publication No. US-2005-0177916-A1) |
|---|---|---|
| Flower color: | Light rose | Rose |
| Habit: | Trailing branches | Long trailing branches |

The family relationship between 'Imtracaro' is: The female parent line of 'Imatracaro' is RBGE 19821569× J475-2 crossed with line H0420. The male parent line of 'Imtracaro' is RBGE 19821569×J475-2 crossed with line M170.

The plant
Parentage:
*Female parent.*—'S3408-1,' not patented.
*Male parent.*—'S2012-1,' not patented.

Propagation:
*Type cutting.*—Terminal cuttings.
*Time to initiate roots.*—10–12 days at 20° C.
*Time to produce a rooted cutting.*—4 weeks.
*Root description.*—Fine, fibrous, and white in color.

Plant description:
*General appearance.*—Makes long branches that tend to grow horizontally.

Habit:
*Growth and branching habit.*—Freely branching habit, freely flowering, and vigorous.
*Plant height.*—24 cm.
*Plant spread.*—81 cm.

Lateral branch description:
*Length.*—10–37 cm.
*Diameter.*—2 mm.
*Texture.*—Smooth, glabrous.
*Internode length.*—About 3.6 cm.
*Color.*—RHS 144A.

Foliage description:
*Arrangement.*—Alternate.
*Length, mature leaves.*—3.7 cm.
*Width, mature leaves.*—2.2 cm.
*Shape.*—Ovate.
*Apex.*—Acuminate.
*Base.*—Attenuate.
*Margin.*—Serrate.
*Texture.*—Smooth, glabrous.
*Venation pattern.*—Pinnate.
*Color young foliage, upper surface.*—RHS 137A.
*Color young foliage, lower surface.*—RHS 137D.
*Fully expanded foliage, upper surface.*—RHS 137A.
*Fully expanded foliage, lower surface.*—RHS 137C.
*Venation, upper surface.*—RHS 137A.
*Venation, lower surface,*—RHS 137C.
*Petiole, length.*—About 1.1 cm.
*Petiole, diameter.*—About 1 mm.
*Petiole, texture.*—Smooth, glabrous.
*Petiole, color.*—RHS 177C.

Flower description:
*Flower type and flowering habit.*—Single.
*Number of flowers per leaf axil.*—2–3.
*Number of flowers and flower buds per lateral branch.*—14–17.
*Flower position.*—Above and beyond the foliage and typically facing upwards and outward.
*Flower shape.*—Rounded, mostly flat.
*Flower lasting about* 7–9 days on the plant depending on environmental conditions.
*Flowers non persistent.*
*Flowers not fragrant.*
*Flower indeterminate and continuous.*
*Flowering season.*—Year round under greenhouse conditions. In the garden, flowering from Spring until Fall.
*Flower diameter.*—About 3.9 cm.
*Flower depth.*—2 mm.

Flower buds:
*Rate of opening.*—From flower bud to fully opened flower, typically about 6–8 days, depending on temperature.
*Bud length* (*at stage of showing color*).—About 1.1 cm.
*Bud diameter.*—About 0.7 cm.
*Bud shape.*—Ellipsoidal.
*Texture.*—Smooth, glabrous.
*Color, just before opening.*—RHS 63C.

Petals:
*Quantity.*—Single, five per flower, imbricate.
*Length of banner petal.*—About 1.5 cm.
*Width of banner petal.*—About 2.1 cm.
*Length, lateral and basal petals.*—About 2.2 cm.
*Width, lateral and basal petals.*—About 1.9 cm.
*Lateral and basal petal shape.*—Obovate.
*Banner petal shape.*—Broadly obcordate.
*Petal apex.*—Retuse to emarginate.
*Petal base.*—Attenuate.
*Petal margin.*—Entire.
*Petal texture.*—Smooth, satiny.
*Petal color.*—Upper surface when opening and fully opened: RHS 66B. Lower surface when opening and fully opened: RHS 68A.

Sepals:
*Lateral sepals.*—2.
*Shape.*—Ovate-lanceolate.
*Apex.*—Acute.
*Base, lower sepal.*—Shallowly navicular.
*Margin.*—Entire.
*Length.*—3–7 mm.
*Width, lower sepal.*—9–11 mm.
*Texture, upper and lower surface.*—Smooth, glabrous.

Spur:
*Length.*—About 2.5 cm.
*Texture.*—Smooth, glabrous.
*Aspect.*—Curved.
*Color.*—RHS 180B.

Peduncles:
*Length.*—About 2–2.5 cm.
*Diameter.*—1 mm.
*Aspect.*—About 45 degrees from the stem.
*Color.*—RHS 181C.

Bracts: At least 2.
*Shape.*—Linear-lanceolate.
*Apex.*—Acute.
*Length.*—3–6 mm.
*Color.*—RHS 177C.

Reproductive organs:
*Androecium.*—Stamen number: five fused at anthers, filaments free, hooded. Anther shape: Oval. Anther length: About 2 mm. Anther color: RHS 63A. Amount of pollen: No pollen.
*Gynoecium.*—Pistil number: One. Pistil length: About 5 mm. Stigma shape: Columnar, five segmented. Stigma color: Red purple. Style color: RHS 64A. Ovary arrangement: Five celled. Ovary color: RHS 147A.

Seed development: Seed development has not been observed.

Disease/pest tolerance: No known susceptibility to disease or insects noted to date.

What is claimed is:

1. A new and distinct cultivar of *Impatiens* plant named 'Imtracaro,' as substantially illustrated and described herein.

* * * * *

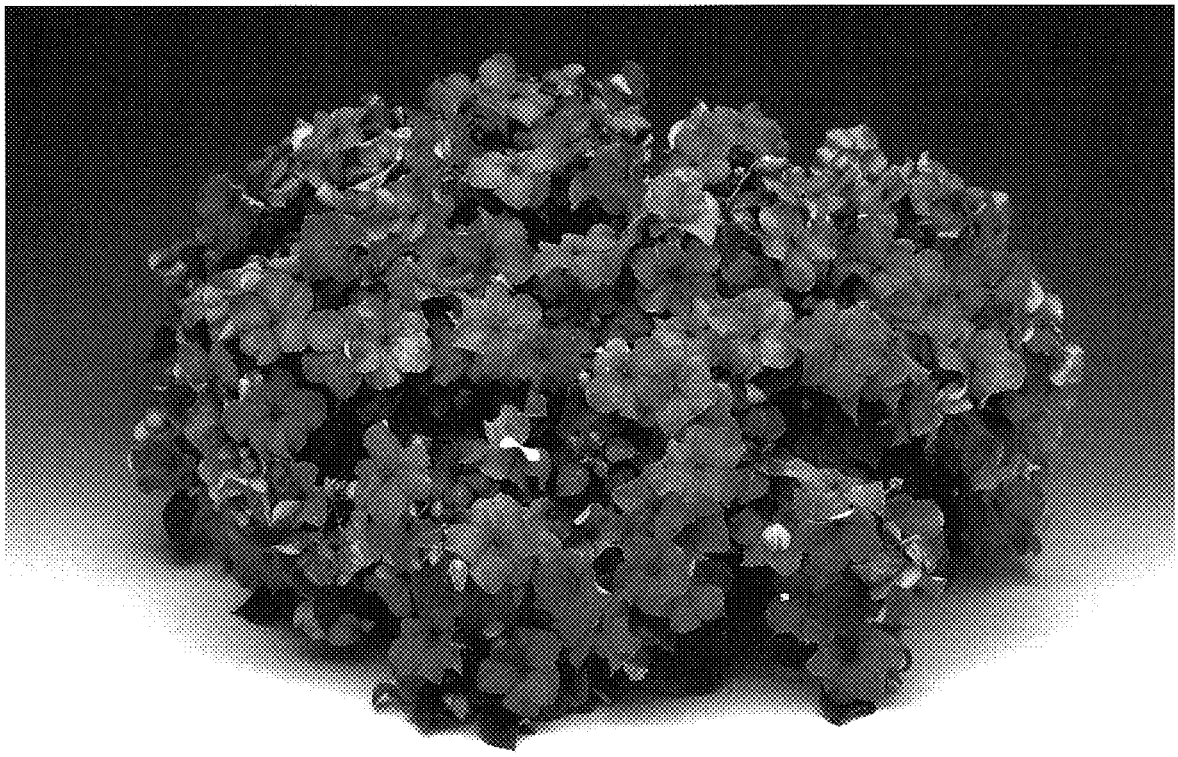

UNITED STATES PATENT AND TRADEMARK OFFICE

CERTIFICATE OF CORRECTION

PATENT NO. : PP 18,579 P2
APPLICATION NO. : 11/585729
DATED : March 11, 2008
INVENTOR(S) : Monica Maria Adelheid Sanders It is certified that error appears in the above-identified patent and that said Letters Patent is hereby corrected as shown below:

At column 2, line 36, delete "M170" and insert therefor --M0170--

At column 3, delete "Flower" and insert therefor --Flowers-- before "indeterminate"

Signed and Sealed this

Seventeenth Day of June, 2008

JON W. DUDAS
*Director of the United States Patent and Trademark Office*